US00PP27326P2

(12) United States Plant Patent
Bacon

(10) Patent No.: US PP27,326 P2
(45) Date of Patent: Nov. 1, 2016

(54) PLUM TREE NAMED 'SUPLUMFORTYNINE'

(50) Latin Name: *Prunus salicina*
Varietal Denomination: Suplumfortynine

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 15 days.

(21) Appl. No.: 14/545,356

(22) Filed: Apr. 27, 2015

(51) Int. Cl.
*A01H 5/08* (2006.01)

(52) U.S. Cl.
USPC ..... Plt./184

(58) Field of Classification Search
USPC ..... Plt./184
See application file for complete search history.

*Primary Examiner* — Annette Para
(74) *Attorney, Agent, or Firm* — Knobbe, Martens, Olson & Bear, LLP

(57) ABSTRACT

A new and distinct plum tree variety, *Prunus salicina*, cv. 'Suplumfortynine' is characterized by fruit having deep red flesh and a cling stone. The fruit is medium in sugar and has medium-low acidity. The fruit of the new variety 'Suplumfortynine' is also moderate in juice and has a sweet-mild flavor. The date of the harvest of the fruit of the new variety is earlier than for 'Early Queen' (U.S. Plant Pat. No. 8,583) and 'Flavorosa' (U.S. Plant Pat. No. 10,285). The fruit of the new variety 'Suplumfortynine' has fruit with deep red flesh compared to yellow colored fruit of 'Early Queen' (U.S. Plant Pat. No. 8,583). The fruit of the new variety 'Suplumfortynine' has red-dappled colored skin compared to dark purple skin of 'Flavorosa' (U.S. Plant Pat. No. 10,285).

1 Drawing Sheet

Latin name of the genus and species claimed: *Prunus salicina.*

Variety denomination: 'Suplumfortynine'.

BACKGROUND AND SUMMARY OF THE INVENTION

This invention relates to the discovery and asexual propagation of a new and distinct variety of plum, *Prunus salicina* cv. 'Suplumfortynine'. The new variety was first originated by hybridization by Terry A. Bacon as breeder number 'PL1346RZ'.

The new variety 'Suplumfortynine' is characterized by having fruit with deep red flesh and a cling stone. The fruit is medium in sugar and has medium-low acidity. The fruit of the new variety 'Suplumfortynine' is also moderate in juice and has a sweet-mild flavor.

The seed parent is 'Suplumthirtyseven' (U.S. Plant Pat. No. 18,690), and the pollen parent is 'PL526YB' (unpatented breeding variety). The parent varieties were first crossed in February 2009, with the date of first sowing being March 2010, and the date of first flowering being February 2011. The new plum variety 'Suplumfortynine' was first asexually propagated by Terry Bacon near Wasco, Kern County, Calif. in January 2012 by grafting.

The new variety 'Suplumfortynine' is distinguished from its seed parent 'Suplumthirtyseven' (U.S. Plant Pat. No. 18,690) in that the new variety 'Suplumfortynine' has fruit with deep red flesh while the fruit of 'Suplumthirtyseven' (U.S. Plant Pat. No. 18,690) has yellow flesh.

The new variety 'Suplumfortynine' is distinguished from its seed parent 'PL526YB' (unpatented breeding variety) in that the new variety 'Suplumfortynine' has fruit with deep red flesh while the fruit of 'PL526YB' (unpatented breeding variety) has yellow flesh.

The fruit of the new variety 'Suplumfortynine' harvest starts May 22 in Wasco, Calif. while 'Earliqueen' (U.S. Plant Pat. No. 8,583) harvest starts May 28. Addtionally, the new variety 'Suplumfortynine' has while fruit with deep red flesh 'Earliqueen' (U.S. Plant Pat. No. 8,583) has yellow flesh. The new variety 'Suplumfortynine' has fruit with deep red flesh similar to 'Flavorosa' (U.S. Plant Pat. No. 10,285) but the skin color of the new variety 'Suplumfortynine' is red-dapple colored while 'Flavorosa' (U.S. Plant Pat. No. 10,285) skin color is dark purple. The new variety 'Suplumfortynine' harvest is on May 22 while 'Flavorosa' (U.S. Plant Pat. No. 10,285) harvest is on May 25.

The new variety 'Suplumfortynine' has been shown to maintain its distinguishing characteristics through successive asexual propagations by, for example, grafting and budding.

BRIEF DESCRIPTION OF THE PHOTOGRAPH

The accompanying color photographic illustration FIG. 1 shows typical specimens of the foliage and fruit of the present new plum variety 'Suplumfortynine'. The illustration shows the upper and lower surface of the leaves, a view of the fruit as a whole, the stone as a whole, and a sectional view of a fruit divided across its suture plane to show flesh color, pit cavity and the stone remaining in place.

The photographic illustration was taken shortly after being picked and the colors are as nearly true as is reasonably possible in a color representation of this type. The photographs depicts fruit and vegetative growth from a three year old tree?

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 3 year old 'Suplumfortynine' plants, grown in the vicinity of Wasco, Kern County, Calif., during 2014 and is believed to apply to plants of the variety grown under similar conditions of soil and climate elsewhere.

TREE

General: (Measurements taken on a 3 year old tree unless otherwise noted.).

*Size*.—Medium, reaches a height of approximately 3 meters including normal pruning.

*Spread*.—Approximately 3 meters.

*Vigor*.—Medium, growth of about 1.8 m to 2 m in height the first growing season.

*Growth*.—Semi-upright.

*Productivity*.—Productive.

*Form*.—Vase formed.

*Bearer*.—Regular.

*Fertility*.—Unknown.

*Canopy density*.—Medium.

*Hardiness*.—Hardy in all fruit growing areas of California. Winter chilling requirement is approximately 700 hours at or below 7.2° C.

*Disease resistance/susceptibility*.—Under close observation in Kern County, Calif., no particular plant/fruit disease resistance/susceptibility has been observed.

*Insect resistance/susceptibility*.—Under close observation in Kern County, Calif., no particular plant/fruit insect resistance/susceptibility has been observed.

Trunk: (Measurements at approximately 30 cm above soil line on mature tree).

*Length*.—45 cm.

*Diameter*.—Approximately 14 cm.

*Texture*.—Medium shaggy, increases with age of tree.

*Trunk color*.—About Medium Greyed-Green 198B on older, weathered wood and about Medium Greyed-Orange 173B in younger, less weathered wood.

Branches: (Measurements at approximately 90 cm above soil line.).

*Length*.—2 m.

*Size*.—Diameter approximately 10 cm.

*Texture*.—Medium, Shaggy.

*Color*.—Varying between about Medium Greyed-Green 198B to about Medium Greyed-Orange 173B, becoming darker with age.

*Lenticels*.—Present.

Lenticels:

*Number*.—Medium. About 1/cm2.

*Density*.—About 2/cm$^2$.

*Color*.—About Medium Grey-Brown 199B.

*Size*.—Medium, approximately 3 mm×2 mm.

Flowering shoots: (Data taken in June at mid-point of current season growth.).

*Size*.—Average diameter approximately 5 mm.

*Color*.—Topside: About Medium Green 141C with highlights of about Medium Greyed-Red 180C. Underside: About Medium Green 141C.

*Internode length*.—Medium; approximately 2 cm. Midway on flowering shoot.

*Flowering shoot lenticels*.—Moderate amount. 3/cm2. Color: About Light Greyed-Orange 164C. Diameter: Approximately 0.5 mm.

*Flowering shoot leaf buds*.—Shape: Conical. Width: Approximately 1.5 mm. Length: Approximately 2 mm. Color: About Medium Greyed-Orange 166C. Texture: Smooth.

*Flowering shoot flower buds*.—Shape: Ovoid. Width: Approximately 1.1 mm. Length: Approximately 2 mm. Color: About Medium Greyed-Orange 166C. Number of buds per node: 2-4. Texture: Smooth.

*Density of buds*.—Medium.

*Flower bud distribution*.—On spurs and one year old shoots and older wood.

*Ratio of wood (leaf) buds to flowering buds*.—½ on nodes.

*Anthocyanin intensity*.—Slightly on upper potion of shoots.

*Spur length*.—Usually 9 mm.

*Vegetative bud size*.—Length 3 mm, width 2 mm.

*Position of vegetative bud in relation to shoot*.—Slightly held out.

FOLIAGE

Leaves: (Data taken in June 10 on fully expanded leaves at mid-point of the current season growth.).

*Average length*.—Medium; approximately 80 mm without petiole.

*Average width*.—Medium; approximately 41 mm.

*Thickness*.—Medium. 1 mm.

*Color*.—Upper surface: About Medium Green 137A. Lower surface: About Medium Green 138A.

*Form*.—Broad obovate.

*Tip*.—Cuspidate.

*Base*.—V-shaped.

*Margin*.—Crenate.

*Venation*.—Pinately net veined.

*Vein color*.—About Medium Green 141C.

*Surface texture*.—Smooth both upper and lower surfaces.

*Leaf blade (ratio of length to width)*.—Medium, about 2:1.

*Shape in the cross section*.—Concave.

*Angle at apex*.—Small.

*Profile*.—Up folded.

*Leaf blade tip*.—Curved downwardly.

*Angle of tip*.—Acute.

*Undulation of margin*.—Slight.

*Glossiness of upper side*.—Slight.

*Density of pubescence of lower side*.—Absent.

Petiole:

*Average length*.—Short; approximately 8 mm.

*Average diameter*.—Medium, approximately 2 mm.

*Color*.—About Medium Green 146D with highlights of about Medium Greyed-Red 180C.

*Thickness*.—Medium, approximately 2 mm.

*Texture*.—Smooth.

*Length*.—11 mm.

Stipules:

*Number/leaf bud*.—Approximately 0-2 per leaf bud when present.

*Typical length*.—Approximately 8 mm.

*Color*.—About Medium Yellow-Green 147C.

*Persistence*.—Falls off.

*Texture* (*upper*).—Smooth upper and lower surfaces.

Leaf glands:

*Average number*.—Approximately 0-2, usually 2.

*Form*.—Globose.

*Positioning*.—Opposite, located near the top of the petiole.

*Size*.—About 1×1 mm.

*Color*.—About Medium Greyed-Orange 166C.

FLOWERS

General:

*Flower blooming period*.—First bloom: Approximately February 6 in Wasco, Calif. Full bloom: Approximately February 10 in Wasco, Calif.

*Location of first bloom*.—Bottom of third canopy.

*Location of full bloom*.—Mid-section of the canopy.

*Duration of bloom*.—Medium; approximately 10 days.

*Diameter of fully opened flower*.—Medium, approximately 14 mm.

*Flower aroma*.—Slight.

*Shape*.—Rosaceous.

Peduncle:

*Length*.—Medium; approximately 8 mm.

*Diameter*.—Medium; approximately 1.2 mm.

*Color*.—About Medium Yellow-Green 144B.

*Pubescence*.—Absent.

Petals:

*Number*.—5.

*Arrangement*.—Overlapping.

*Length*.—Approximately 5 mm.

*Diameter*.—Approximately 5 mm.

*Shape*.—Circular.

*Apex shape*.—Rounded.

*Base shape*.—Narrows at point of attachment.

*Color of inner and outer surface*.—About White 155B.

*Surface texture*.—Smooth.

*Margins*.—Slightly undulating, entire.

*Frequency of flowers with double petals*.—None.

*Claw length*.—Short, 2 mm.

*Margin waviness*.—Medium.

*Base angle*.—Medium.

*Division of upper margin*.—Entire.

*Pubescence of inner surface*.—Absent.

*Pubescence of outer surface*.—Absent.

Sepals:

*Number*.—5.

*Length*.—Approximately 3 mm.

*Diameter*.—Approximately 3 mm.

*Shape*.—Triangular.

*Color*.—About Light Yellow-Green 144D.

*Surface texture*.—Smooth.

*Margins*.—Finely toothed.

*Positioning*.—Adpressed to petals.

*Pubescence of inner surface*.—Absent.

*Pubescence of outer surface*.—Absent.

*Frequency of flowers with double sepals*.—None.

Stamens:

*Number*.—Usually 26-32, average 29.

*Average length*.—About 3-6 mm, average about 5 mm.

*Filament color*.—About White 155B.

*Anther color*.—About Light Yellow-Orange 18D, becoming dark as it ages to Dark Yellow-Orange 22A.

*Flower pollen color*.—About Dark Yellow-Orange 22A.

*Position*.—Perigynous.

Pistil:

*Color*.—Yellow-Green 144C.

*Number*.—Usually one.

*Average length*.—Approximately 8 mm.

*Ovary diameter*.—Approximately 1 mm.

*Pubescence*.—None.

*Stigma extension in comparison to anthers*.—Usually below.

*Style frequency of supplementary pistils*.—Few.

Flower-buds:

*Hardiness*.—Somewhat hardy.

Receptacle:

*Depth*.—Medium, 4 mm.

*Pubescence of inner surface*.—Absent.

*Pubescence of outer surface*.—Absent.

Ovary:

*Color*.—Yellow-Green 144C.

Style:

*Pubescence* (*of base*).—Absent.

FRUIT

General: (Description taken near Wasco, Kern County, Calif. on May 26).

*Date of first pick*.—Approximately May 22.

*Date of last pick*.—Approximately June 1.

*Maturity when described*.—Firm.

*Season ripening*.—Very early. Starting about May 22 and continuing until June 1.

*Position of maximum diameter*.—Towards the middle.

*Symmetry about the suture*.—Symmetric.

*Shape of base*.—Flat.

Size:

*Length* (*stem end to apex*).—Approximately 58 mm.

*Diameter in line with suture plane*.—Approximately 63 mm.

*Diameter perpendicular to suture plane*.—Approximately 63 mm.

*Average weight*.—Approximately 118 gm.

Form:

*Viewed from apex*.—Rounded.

*Viewed from side, facing suture*.—Rounded.

*Viewed from side, perpendicular to suture*.—Rounded.

Apex shape: Rounded.

Fruit stem cavity:

*Shape*.—Rounded.

*Depth*.—Shallow; Approximately 7 mm.

*Breadth*.—Approximately 6 mm.

*Width*.—Medium, 14 mm.

Fruit stem:

*Length*.—Medium; approximately 8 mm.

*Diameter*.—Approximately 3 mm.

*Color*.—About Light-Yellow-Green 147D.

*Adherence to stone*.—Strong.

Fruit skin:

*Thickness*.—Medium, 0.8 mm.

*Adherence to flesh*.—Strong.

*Surface texture*.—Smooth.

*Pubescence*.—None.

*Bloom*.—Light.

*Ground color*.—About Medium Greyed-Red 184A where visible.

*Overcolor*.—About Dark Greyed-Purple 187A.
*Relative area of overcolor*.—Nearly 100%.
*Pattern of overcolor*.—Solid.
*Taste*.—Midly-tart.
*Reticulation*.—Absent.
*Roughness*.—Absent.
*Tenacity*.—Tenacious to flesh.
*Tendency to crack*.—Slight to none in wet season.

Flesh:
*Ripens*.—Evenly.
*Texture*.—Firm-juicy.
*Fibers*.—Few.
*Flavor*.—Sweet-mild.
*Brix*.—Approximately 16°.
*Juice*.—Moderate.
*Aroma*.—Slight.
*Anthocyanin color around stone*.—About Dark Red 46A.
*Anthocyanin color of flesh*.—Strongly expressed throughout evenly.
*Amygdalin*.—Wanting.
*Acidity*.—Medium-low.
*Sugar content*.—High.
*Eating quality*.—Good.
*Stone/flesh ratio*.—Small, about 1:98.
*Firmness*.—Medium.

Pit cavity size:
*Length*.—Approximately 25 mm.
*Diameter perpendicular to suture plane*.—Approximately 20 mm.
*Diameter in line with suture*.—Approximately 9 mm.
*Color*.—About Dark Red 46A.

Fruit use: Fresh market.
Fruit shipping and keeping quality: Good.

Stone:
*Stone freeness*.—Cling over the entire surface.
*Degree of adherence to flesh*.—Strong.
*Stone size*.—Size: Medium. Size compared to Fruit: Small. Length: Medium, approximately 25 mm. Diameter in line with suture plan: Approximately 20 mm. Diameter perpendicular to suture plane: Approximately 9 mm. Width of Stalk End: Medium, Approximately 3 cm. Angle of Stalk end: Right angle. Hilum: Oval.
*Stone form*.—Viewed from side: Oval with flat base and pointed apex. Viewed from ventral end: Flattened. Viewed from Stem end: Oval.
*Stone shape*.—Base shape: Nearly straight. Apex shape: Pointed.
*Hilum*.—Oval.
*Stone surface*.—Irregularly furrowed and pitted throughout.
*Stone halves*.—Nearly symmetrical.
*Stone ridges*.—Rounded throughout.
*Stone outgrowing keel*.—Well developed.
*Stone tendency to split*.—None in wet season.
*Stone color*.—About Medium Greyed-Orange 164C.
*Position of maximum*.—Middle.
*Sides*.—Somewhat equal.
*Pits*.—Irregular, shallow.
*Ventrical edge*.—Thin with slight wing toward middle.
*Dorsal edge*.—Ridges on either side, throughout.

What is claimed is:

1. A new and distinct plum tree as herein described and illustrated.

* * * * *

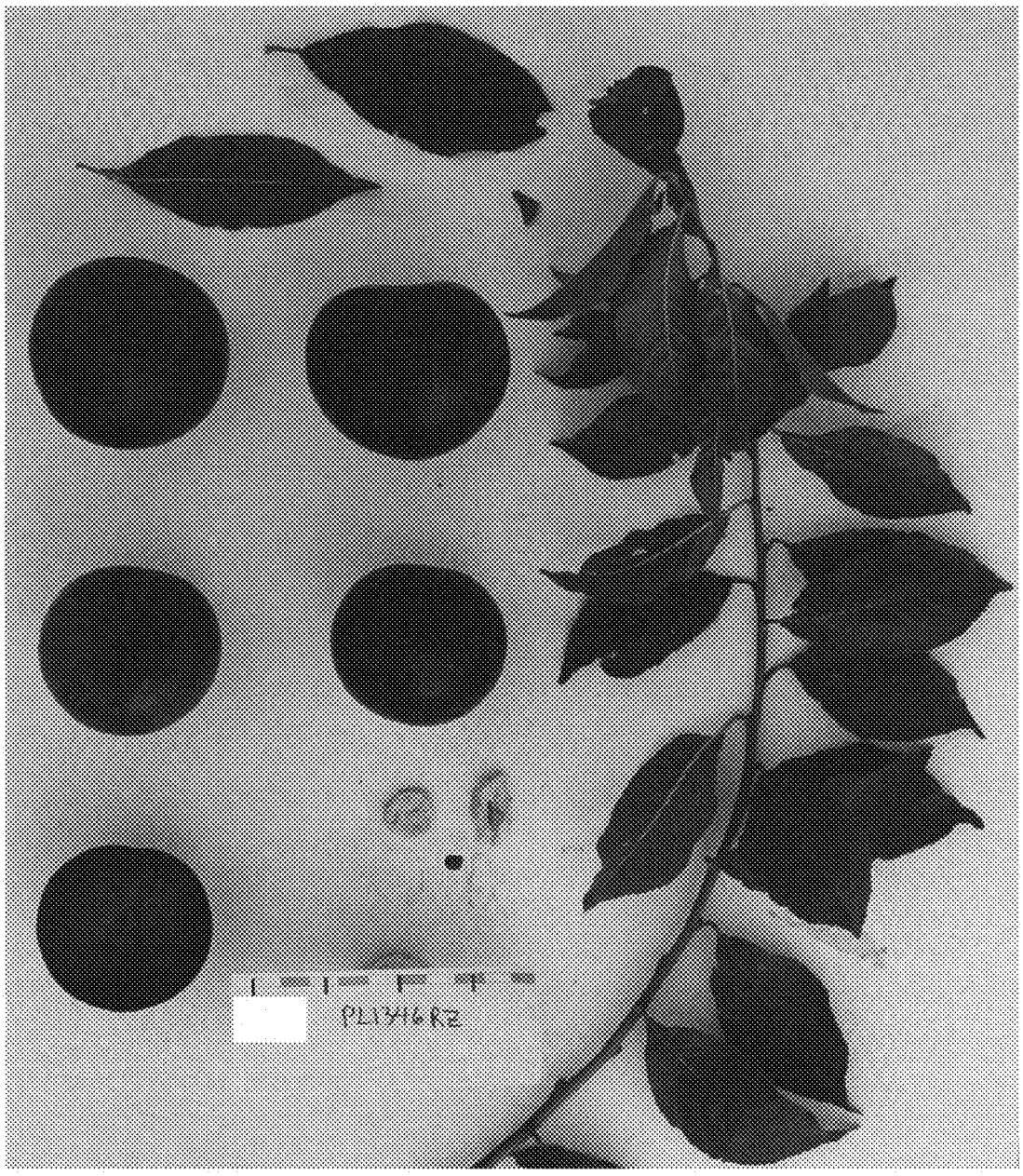
PL1Y16R2